United States Patent
Jian et al.

(10) Patent No.: US 9,968,304 B2
(45) Date of Patent: May 15, 2018

(54) DETECTING A VASOACTIVE AGENT IN THE BLOODSTREAM

(71) Applicant: Edwards Lifesciences Corporation, Irvine, CA (US)

(72) Inventors: Zhongping Jian, Irvine, CA (US); Feras Hatib, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 830 days.

(21) Appl. No.: 14/350,332

(22) PCT Filed: Oct. 5, 2012

(86) PCT No.: PCT/US2012/059101
§ 371 (c)(1),
(2) Date: Apr. 7, 2014

(87) PCT Pub. No.: WO2013/052896
PCT Pub. Date: Apr. 11, 2013

(65) Prior Publication Data
US 2014/0235971 A1 Aug. 21, 2014

Related U.S. Application Data

(60) Provisional application No. 61/544,971, filed on Oct. 7, 2011.

(51) Int. Cl.
*A61B 5/1455* (2006.01)
*A61B 5/00* (2006.01)
(Continued)

(52) U.S. Cl.
CPC ............ *A61B 5/7278* (2013.01); *A61B 5/021* (2013.01); *A61B 5/0205* (2013.01);
(Continued)

(58) Field of Classification Search
CPC ... A61B 5/02007; A61B 5/0205; A61B 5/021; A61B 5/02108; A61B 5/029
See application file for complete search history.

(56) References Cited

U.S. PATENT DOCUMENTS 4,190,886 A * 2/1980 Sherman ................ A61B 5/021
128/900
5,400,793 A 3/1995 Wesseling
(Continued)

FOREIGN PATENT DOCUMENTS

WO 00/57776 A1 10/2000

OTHER PUBLICATIONS

Gray et al (Effect of Nitric Oxide Donors on Blood Pressure and Pulse Pressure in Acute and Subacute Stroke, 2006, Journal of Stroke and Cerebrovascular Diseases, 15(6): 245-249).*
(Continued)

*Primary Examiner* — Christian Jang
*Assistant Examiner* — Angeline Premraj
(74) *Attorney, Agent, or Firm* — Farjami & Farjami LLP.; Farshad Farjami

(57) ABSTRACT

A system and method are disclosed for detecting a vasoactive agent in patient's bloodstream. In one embodiment, an input signal is received that is associated with arterial blood pressure. A change of an arterial blood pressure parameter over time is determined. A vasoactive agent is then automatically detected using the determined change. In another embodiment, a waveform associated with an arterial blood pressure signal can be received. A parameter associated with the received waveform is calculate. Then the calculated parameter can be used to determine the presence of a vasoactive agent. In yet another embodiment, detection of a vasoactive agent in any of the other embodiments can be used in a calculation of a hemodynamic parameter, such as (Continued)

cardiac output, stroke volume, systemic vascular resistance, stroke volume variation, cardiac index, stroke volume index, systemic vascular resistance index, vascular compliance, and vascular tone.

12 Claims, 8 Drawing Sheets

(51) Int. Cl.
    *A61B 5/021*     (2006.01)
    *A61B 5/145*     (2006.01)
    *A61B 5/02*     (2006.01)
    *A61B 5/0205*     (2006.01)
    *A61B 5/029*     (2006.01)
    *A61B 8/08*     (2006.01)
    *A61B 5/0215*     (2006.01)
    *A61B 5/022*     (2006.01)

(52) U.S. Cl.
    CPC .......... *A61B 5/02007* (2013.01); *A61B 5/029* (2013.01); *A61B 5/14546* (2013.01); *A61B 5/14551* (2013.01); *A61B 8/488* (2013.01); *A61B 5/022* (2013.01); *A61B 5/0215* (2013.01); *A61B 5/02108* (2013.01)

(56) References Cited

U.S. PATENT DOCUMENTS

| | | | |
|---|---|---|---|
| 5,535,753 | A | 7/1996 | Petrucelli et al. |
| 6,152,881 | A | 11/2000 | Raines et al. |
| 6,293,915 | B1* | 9/2001 | Amano ............... A61B 5/021 600/485 |
| 6,616,613 | B1* | 9/2003 | Goodman ............ A61B 5/0002 600/300 |
| 7,601,123 | B2 | 10/2009 | Tweed et al. |
| 2003/0199775 | A1* | 10/2003 | Narimatsu ......... A61B 5/02007 600/490 |
| 2005/0222514 | A1* | 10/2005 | Sugo ................... A61B 5/029 600/526 |
| 2005/0267380 | A1* | 12/2005 | Poezevara ........... A61B 5/0809 600/529 |
| 2009/0326353 | A1* | 12/2009 | Watson ............. A61B 5/14551 600/330 |
| 2010/0081944 | A1* | 4/2010 | Baker, Jr. ............... A61B 5/021 600/485 |

OTHER PUBLICATIONS

Kelly et al (Vasoactive Drugs Influence Aortic Augmentation Index Independently of Pulse-Wave Velocity in Healthy Men, 2001, Hypertension, 37:1429-1433).*
Jankowski et al (Ascending aortic blood pressure waveform may be related to the risk of coronary artery disease in women, but not in men, 2004, Journal of Human Hypertension, 18: 643-648).*
Weingart (Upstairs Care Downstairs, 2010, ACEP News, Web, Retrieved from: https://www.acep.org/ClinicalPracticeManagement/UpstairsCareDownstairs/).*
Tallaj et al, The Management of Acute Decompensated Heart Failure, 2003, Web, Retrieved from: http://www.fac.org.ar/tcvc/llave/c038/bourge.htm.*
Yasuno et al, Is Pulse Pressure a Predictor of New-Onset Diabetes in High-Risk Hypertensive Patients?, 2010, Diabetes Care, 33(5): 1122-1127.*
Johnson, PDQ Pharmacology, 2002, Hamilton: B.C. Decker.*
Saba, Your Heart Rate & Training, 2004, Web, Retrieved from: https://web.archive.org/web/20040615201927/http://www.willingtonkarateclub.org/articles/heartrate.html.*
Rich et al, The Effects of Phenylephrine on Right Ventricular Performance in Patients with Pulmonary Hypertension, 1990, Chest, 98(5): 1102-1106.*
Takazawa, et al., Assessment of Vasoactive Agents and Vascular Aging by the Second Derivative of Photoplethysmogram Waveforms, Hypertension, Lippincott Williams & Wilkins, US, vol. 32, No. 2, Aug. 1, 1998, pp. 365-370.
Cohn, et al., Noninvasive Pulse Wave Analysis for the Early Detection of Vascular Disease, Hypertension, Lippincott Williams & Wilkins, US, vol. 26, No. 3, Sep. 1, 1995, pp. 503-508.
Arnsparger et al., Adaptive Control of Blood Pressure, IEEE Transactions on Biomedical Engineering, IEEE Service Center, Piscataway, NJ, USA, vol. BME-19, No. 3, Mar. 1, 1983, pp. 168-176.
International Search Report, dated Jan. 29, 2013.
Office Action issued in EP12783435.6, dated May 22, 2017.

* cited by examiner

DETECTING A VASOACTIVE AGENT IN THE BLOODSTREAM

FIELD

The present application relates to arterial blood pressure and, in particular, to detecting a vasoactive agent using a measurement of arterial blood pressure.

BACKGROUND

Cardiac output (CO) and Stroke volume (SV) are indicators not only for diagnosis of disease, but also for "real-time" monitoring of patients. Few hospitals are, therefore, without some form of equipment to monitor one or more of these cardiac parameters. Both invasive and non-invasive techniques are available.

Most of the techniques used to measure SV can usually be readily adapted to provide an estimate of CO as well, as CO is generally defined as SV times the heart rate HR. Conversely, most devices that estimate CO also estimate SV as a sub-step. As is explained in greater detail below, still another cardiac parameter that promises to provide clinically important information is stroke volume variation SVV. One way to estimate SVV is simply to collect multiple SV values and calculate the differences from measurement interval to measurement interval.

One common way to measure SV or CO is to mount some flow-measuring device on a catheter, and then to thread the catheter into the subject and to maneuver it so that the device is in or near the subject's heart. Some such devices inject either a bolus of material or energy (usually heat) at an upstream position, such as in the right atrium, and determine flow based on the characteristics of the injected material or energy at a downstream position, such as in the pulmonary artery.

Still other invasive devices are based on the known Fick technique, according to which CO is calculated as a function of oxygenation of arterial and mixed venous blood.

Invasive techniques have obvious disadvantages. For example, catheterization of the heart is potentially dangerous, especially considering that the patients typically have a serious condition. Moreover, some catheterization techniques, most notably thermodilution, rely on assumptions, such as uniform dispersion of the injected heat, that affect the accuracy of the measurements depending on how well they are fulfilled. Moreover, the very introduction of an instrument into the blood flow may affect the value (for example, flow rate) that the instrument measures.

Doppler techniques, using invasive as well as non-invasive transducers, are also used to measure flow and to calculate SV and CO from the flow measurements. Not only are these systems typically expensive, but their accuracy depends on precise knowledge of the diameter and general geometry of the flow channel Such precise knowledge is, however, seldom possible, especially under conditions where real-time monitoring is desired.

One blood characteristic that has proven particularly promising for accurately determining parameters, such as CO, SV, and SVV with minimal or no invasion is blood pressure. Most known blood-pressure-based systems rely on the so-called pulse contour method (PCM), which calculates an estimate of the cardiac parameter(s) of interest from characteristics of the beat-to-beat pressure waveform. In the PCM, "Windkessel" (German for "air chamber") parameters (characteristic impedance of the aorta, compliance, and total peripheral resistance) are typically used to construct a linear or non-linear, hemodynamic model of the aorta. In essence, blood flow is analogized to a flow of electrical current in a circuit in which an impedance is in series with a parallel-connected resistance and capacitance (compliance). The three required parameters of the model are usually determined either empirically, through a complex calibration process, or from compiled "anthropometric" data, i.e., data about the age, sex, height, weight, and/or other parameters of other patients or test subjects. U.S. Pat. No. 5,400,793 (Wesseling, 28 Mar. 1995) and U.S. Pat. No. 5,535,753 (Petrucelli, et al., 16 Jul. 1996) discloses systems that rely on a Windkessel circuit model to determine CO.

PCM-based systems can monitor SV-derived cardiac parameters using blood pressure measurements taken using a variety of measurement apparatus, such as a finger cuff, and can do so more or less continuously. This ease of use comes at the potential cost of accuracy, however, as the PCM can be no more accurate than the rather simple, three-parameter model from which it was derived. A model of a much higher order would be needed to faithfully account for other phenomena. Many improvements, with varying degrees of complexity, have been proposed for improving the accuracy of the basic PCM model.

Vasoactive agents (such as vasoconstrictors, vasodilators, and inotropes) have an impact on vascular tone (vascular compliance and resistance), which usually induces changes in blood pressure. As a result, this could have a negative impact on blood-pressure-based systems that measure CO and introduces errors on the measurement parameters, such as CO, SV, SVR and SVV. Vasoactive agents are a group of bioactive chemicals, which change vasomotor tone through their influence on various peripheral receptors. Most of these agents have inotropic effects (e.g. norepinephrine) as they bind with receptors positioned on the surface of the myocardium. Vasoactive drugs generally affect stroke volume and heart rate, and, thus, determine cardiac output and overall cardiovascular function. When vasoactive drugs are present, CO, SV, and SVV measurements are often inaccurate.

SUMMARY

A system and method are disclosed for detecting a vasoactive agent in patient's bloodstream using arterial blood pressure.

In one embodiment, an input signal is received that is associated with arterial blood pressure. A change of a parameter over time is determined. A vasoactive agent is then automatically detected using the determined change.

The arterial blood pressure can be measured invasively or non-invasively to produce the input signal. Additionally, the vasoactive agent can be a vasoconstrictor, vasodilator, or inotrope. Example vasoactive agents include Phenylephrine, Epinephrine, Ephedrine, Nitroprusside, Dobutamine, Nitroglycerin, Hydralazine, Trimethaphan, Norepinephrine, Dopamine, Isoproterenol, Amrinone, Milrinone, and Digoxin, but also other vasoactive agents can be detected. Naturally occurring vasoactive agents can also be detected and include, but are not limited to, adrenaline, noradrenaline, histamine, nitric oxide, adrenocorticotrophin (ACTH), vasopressin, etc.

In another embodiment, a waveform associated with an arterial blood pressure signal can be received. A parameter associated with the received waveform can be calculated. Then the calculated parameter can be used to determine the presence of a vasoactive agent.

The calculated parameter can be selected from pulse pressure, standard deviation of pressure waveform, the area under the systolic phase of the arterial pressure waveform (systolic area), the area under the diastolic phase of the arterial pressure waveform (diastolic area), mean arterial pressure, systolic pressure, diastolic pressure, pressure at a specific time point in each heartbeat, differentiation of pressure with respect to time, time durations of specific phases of the arterial pressure waveform (systolic phase, systolic rise, systolic decay, diastolic phase, diastolic time constant, . . . etc), heart rate (or pulse rate), measures of the morphological parameters of the arterial pressure waveform, or a combination thereof.

In yet another embodiment, detection of a vasoactive agent in any of the other embodiments can be used in a calculation of a hemodynamic parameter, such as cardiac output, stroke volume, systemic vascular resistance, stroke volume variation, pulse pressure or systolic pressure variations, cardiac index, stroke volume index, systemic vascular resistance index, vascular compliance, and vascular tone. Such a calculation using the information of the vasoactive agent provides a significant advantage over prior calculations, which neglect the use of the vasoactive agent.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The foregoing and other objects, features, and advantages of the invention will become more apparent from the following detailed description, which proceeds with reference to the accompanying figures.

DETAILED DESCRIPTION

Figure 1:
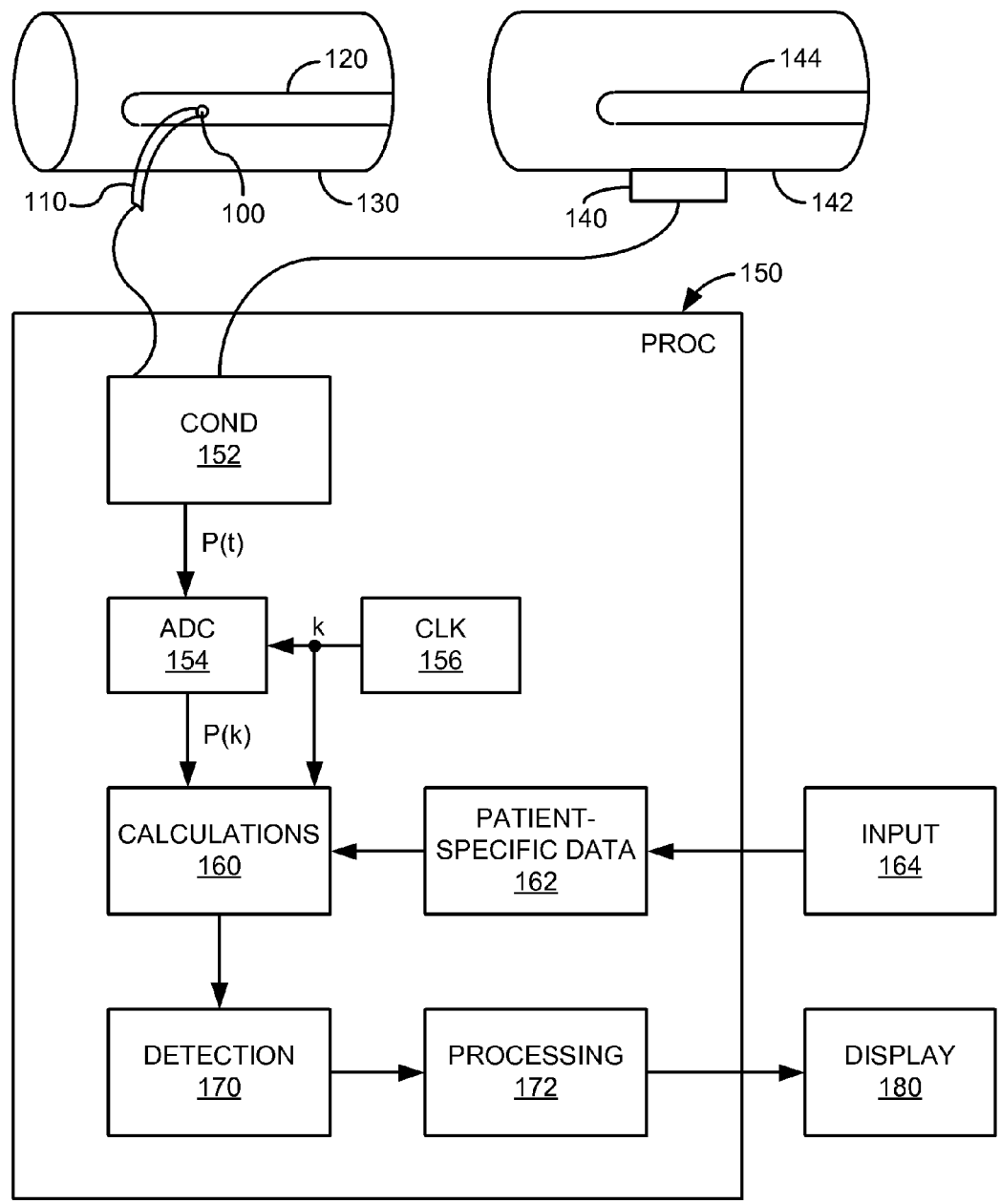
FIG. 1 is an example system diagram illustrating different components that can be used for detecting a vasoactive agent in a patient's bloodstream.

FIG. 1 shows the main components of a system that can be used to implement the methods described herein for detecting a vasoactive agent in the bloodstream of a patient. Pressure, or some other input signal proportional to pressure, may be sensed either invasively or non-invasively, or both. For convenience, the system is described as measuring arterial blood pressure as opposed to some other input signal that is converted to pressure. Alternative systems can be used, as is well understood in the art.

FIG. 1 shows both types of pressure sensing for the sake of completeness. In most practical applications of the methods described herein, either one or several variations can be implemented. In invasive applications, a conventional pressure sensor 100 can be mounted on a catheter 110, which is inserted in an artery 120 of a patient body part 130. The artery 120 is any artery in the arterial system, such as, for example, the femoral, radial or brachial artery. In the non-invasive applications, a conventional pressure sensor 140, such as a photo-plethysmographic or a blood pressure probe, is mounted externally in any manner, for example, using a cuff around a finger 142 or a transducer mounted on the wrist of the patient to read blood pressure of an artery 144.

The signals from the sensors 100 and/or 140 are passed via any known connectors as inputs to a processing system 150, which includes one or more processors and other supporting hardware and system software (not shown) usually included to process signals and execute code. The methods described herein may be implemented using a modified personal computer, or may be incorporated into a larger, specialized monitoring system. For use with the methods described herein, the processing system 150 can include, or is connected to, conditioning circuitry 152, which performs normal signal processing tasks, such as amplification, filtering, or ranging, as needed. The conditioned, sensed input pressure signal P(t) can then be converted to digital form by a conventional analog-to-digital converter ADC 154, which can take a signal reference from a clock circuit 156. As is well understood, the sampling frequency of the ADC 154 can be chosen with regard to the Nyquist criterion so as to avoid aliasing of the pressure signal, which is known in the art of digital signal processing. The output from the ADC 154 can be the discrete pressure input signal P(k), whose values may be stored in conventional memory circuitry (not shown).

The values P(k) can be passed to or accessed from memory by a software, hardware, or firmware module 160. For example, module 160 can comprise computer-executable code for calculating parameters associated with a pulsatility of the pressure input signal. The pulsatility parameters can be calculated at multiple points in time and can be any desired parameter. Example parameters include pulse pressure, standard deviation of pressure waveform, systolic area, diastolic area, mean arterial pressure, systolic pressure, diastolic pressure, pressure at a specific time point in each heartbeat, differentiation of pressure with respect to time, or a combination of these different parameters. If desired, patient-specific data, such as age, height, weight, BSA, etc., can be stored in a memory region 162 (other predetermined parameters, such as threshold or threshold range values can also be stored). Predetermined pulsatility data can also be stored in the memory region 162, so that measurements can be based on historic patient data. Any of the above-described values may be entered using any known input device 164 in the conventional manner Detection of a vasoactive agent can be accomplished in detection module 170. Detection module 170 can include computer-executable code that can analyze calculations made in module 160 and perform the analysis for detection of a vasoactive agent, as further described below. As illustrated by FIG. 1, the results can be passed to further modules 172 for additional processing. Alternatively, the additional processing can be performed within the detection module. In any event, the additional processing can include a calculation of a hemodynamic parameter. In such a calculation, whether or not a vasoactive agent was present can be used. The hemodynamic parameter can be associated with a wide variety of cardiovascular-related elements, such as cardiac output, stroke volume, systemic vascular resistance, stroke volume variation, cardiac index, stroke volume index, systemic vascular resistance index, vascular compliance, and vascular tone. The results can be displayed on a conventional display or recording device 180 for presentation to and interpretation by a user.

Figure 2:
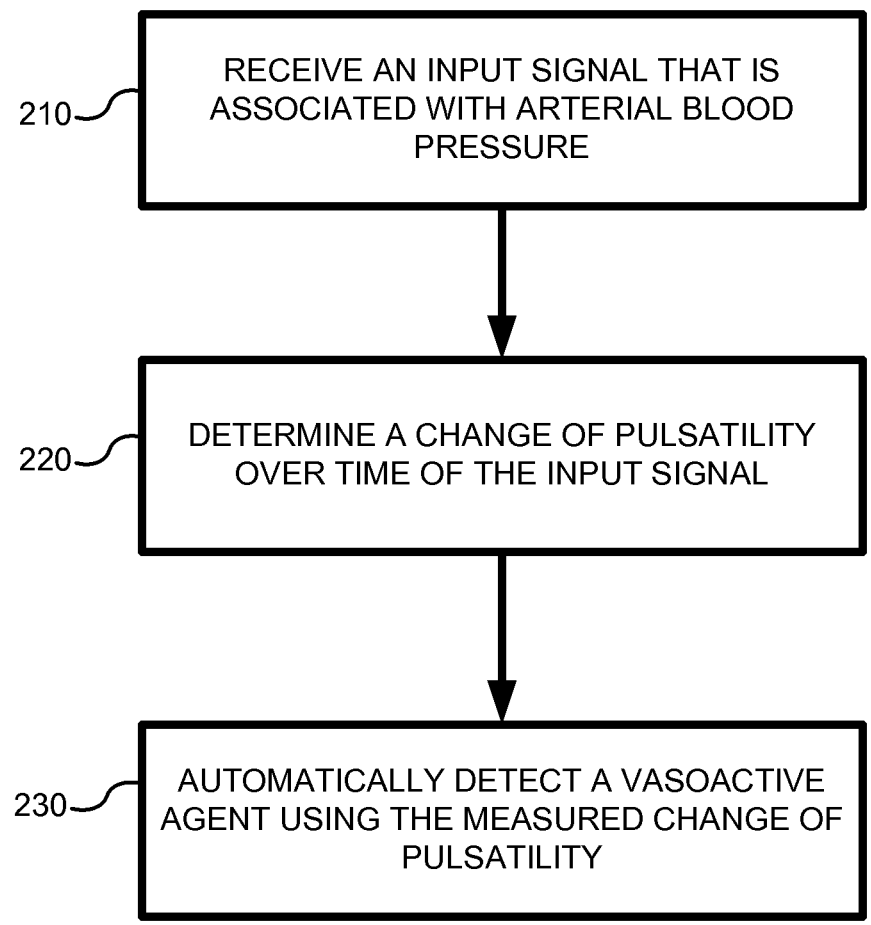
FIG. 2 is a flowchart of a method for detecting a vasoactive agent in a patient's bloodstream.

FIG. 2 shows a flowchart of an exemplary method for detecting a vasoactive agent. In process block 210, an input signal is received that is associated with arterial blood pressure. The input signal can be received by an apparatus, such as is shown in FIG. 1, or other desired apparatus, as is well understood in the art. The input signal can be proportional to, or derived from arterial pressure, flow rate, vascular resistance, pulse oximetry, Doppler ultrasound, bioimpedance signal, or related measurements or signals. The input signal can be in a variety of formats, such as a waveform, a digitized signal, or an analog signal. In process block 220, a change of pulsatility is determined over a period of time of the input signal. Pulsatility is generally known in the art to be a change in a pulse signal in response to each cardiac contraction. The period of time can be any desired period. Some example periods include any time between 1.0 and 60 minutes, but other time limits can be used. In process block 230, a vasoactive agent can be automatically detected using the measured change of pulsatility. Automatic detection can be achieved using hardware, software, or firmware components, such as shown in FIG. 1. The vasoactive agent can be a vasoconstrictor, a vasodilator, or an inotrope. Example vasoactive agents include, but are not limited to Phenylephrine, Epinephrine, Ephedrine, Nitroprusside, etc.

Figure 3:
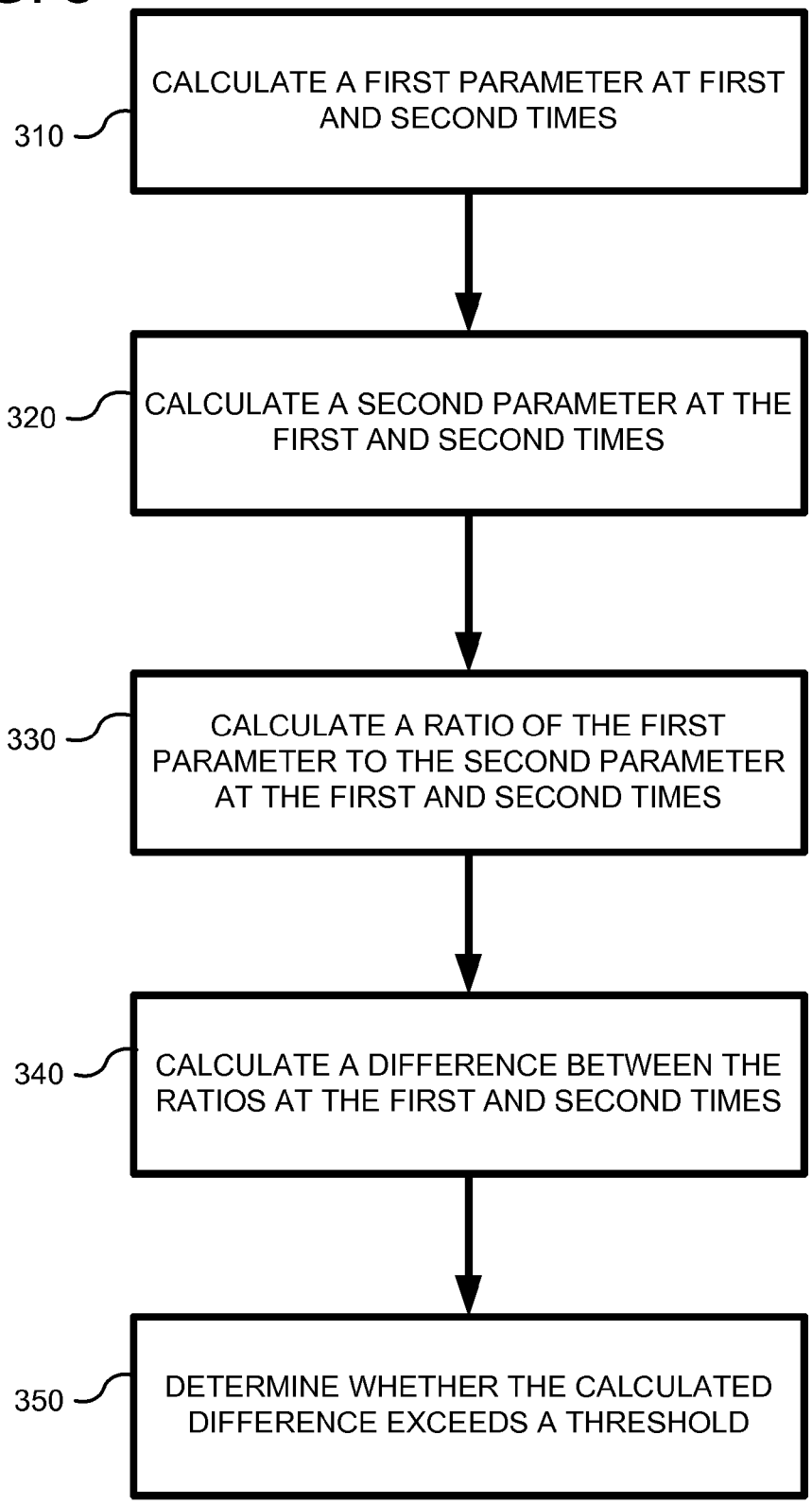
FIG. 3 is a more detailed flowchart of an embodiment for detecting a vasoactive agent.

FIG. 3 shows a flowchart of a particular embodiment that can be used to determine a change of pulsatility and to detect the vasoactive agent. In process block 310, a first parameter can be calculated at first and second times. A variety of parameters can be used. Example parameters can include pulse pressure, standard deviation of pressure waveform, systolic area, or diastolic area. In process block 320, a second parameter can be calculated at first and second times Like the first parameter, a variety of parameters can be used, such as mean arterial pressure, systolic pressure, diastolic pressure, pressure at a specific time point in each beat, differentiation of pressure with respect to time, systolic area, diastolic area, or a combination thereof. The first and second times can be at any desired time interval apart. Additionally, the first and second times can be averages over first and second time periods. The process block 330 performs mathematical comparison of the first parameter and the second parameter. In one example, the mathematical comparison is performed by calculating the ratio of the first parameter to the second parameter at the first and second times. Alternative waves to perform mathematical comparison could be used as well. The ratio can alternatively be the second parameter to the first parameter. In process block 340, a difference between the ratios at the first and second times is calculated. The difference or comparison allows for a determination of how the ratio changes with respect to time. In process block 350, a determination is made whether the calculated difference exceeds a predetermined threshold. As described further below, the presence of a vasoactive agent can result in a change in arterial blood pressure parameters. The threshold allows for minor variations in such parameters to be ignored, whereas changes that exceed a predetermined limit are indicative of the presence of a vasoactive agent.

Figure 4:
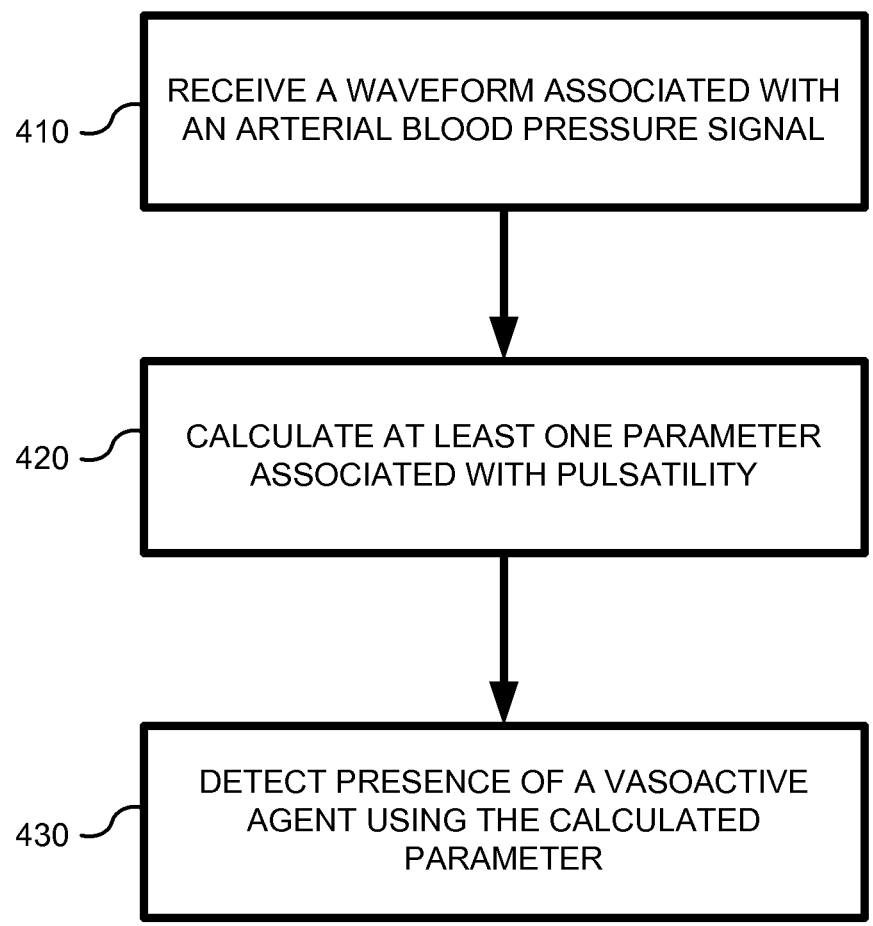
FIG. 4 is a flowchart of another embodiment for detecting a vasoactive agent.

FIG. 4 is a flowchart of another embodiment, wherein detection is not necessarily based on determining a change over time of an input signal. Rather, a parameter associated with pulsatility can be used to detect the presence of a vasoactive agent. In process block 410, an input signal, such as a waveform, is received that is associated with an arterial blood pressure signal. The received waveform can be in a variety of formats, such as digital or analog data which when plotted represents a waveform. In process block 420, at least one parameter associated with the pulsatility is calculated using the received waveform. Calculation of such a parameter is well known in the art. In process block 430, the vasoactive agent is detected using the calculated parameter. Any of the above-identified parameters can be used in the calculation. Moreover, any of the methods of FIGS. 2 and 3 can be used to expand the method of claim 4.

Figure 5:
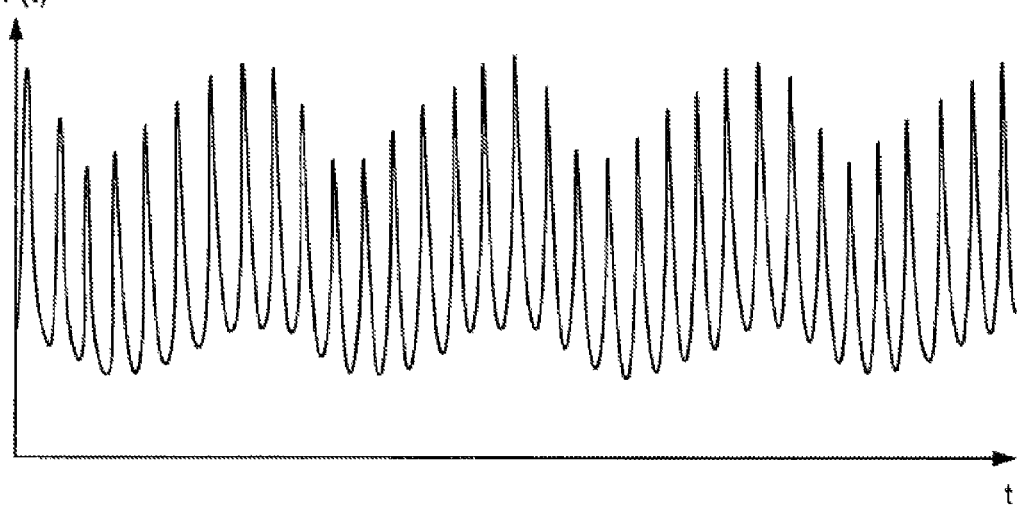
FIG. 5 is an exemplary waveform showing pulsatility of a signal associated with arterial pressure of a patient.

FIG. 5 illustrates a sequence of measured or otherwise acquired arterial pressure waveforms over approximately three respiratory cycles. In practice, the sequence can be a data set P(k) derived from a sampled measurement of arterial pressure P(t). The P(k) values can be obtained through direct, invasive or non-invasive measurement, or may be input from some other source, such as from a remote monitor or even a pre-recorded data set. Pulsatility can be calculated using one or more of the following techniques on the received input signal: integral analysis, correlation, Fourier analysis, maximum-minimum, derivative, or standard deviation.

Figure 6:
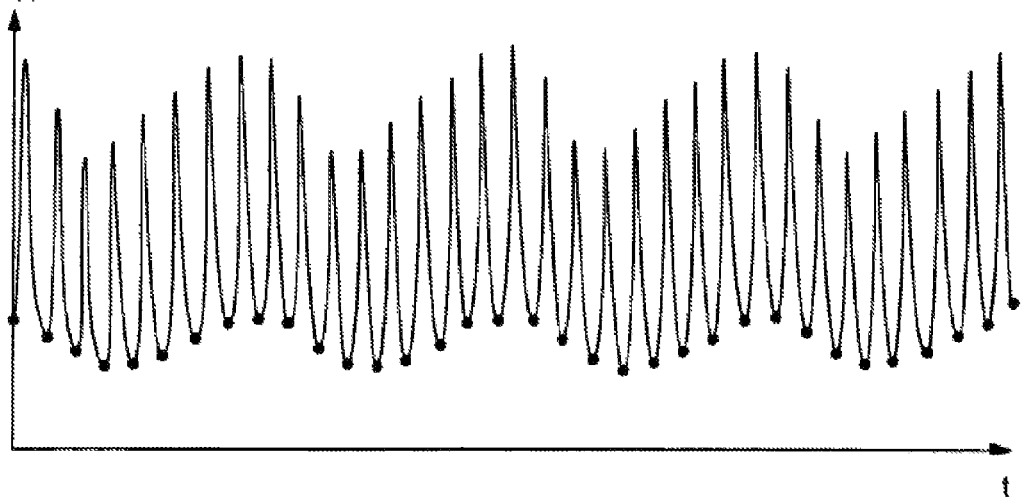
FIG. 6 is an exemplary waveform showing heartbeats associated with pulsatility.

In FIG. 6, dots are included in the waveform of FIG. 5 to indicate the beginning of each cardiac cycle (that is, each "beat") over the illustrated computation interval. The beginning of each cardiac cycle can be determined in any of a number of known ways using any known system that is or includes a heart rate monitor. Assuming, for example, as is often the case, that the patient's cardiac electrical activity is also being monitored by an electrocardiogram system (EKG), then the beginning of each cardiac cycle may be determined to occur at the sampled pressure value immediately following each R-wave. Pressure-based, pulse-rate monitors may also be used and are in fact preferred because they will then be better synchronized with the blood pressure signal than will, for example, an EKG signal.

Figure 7:
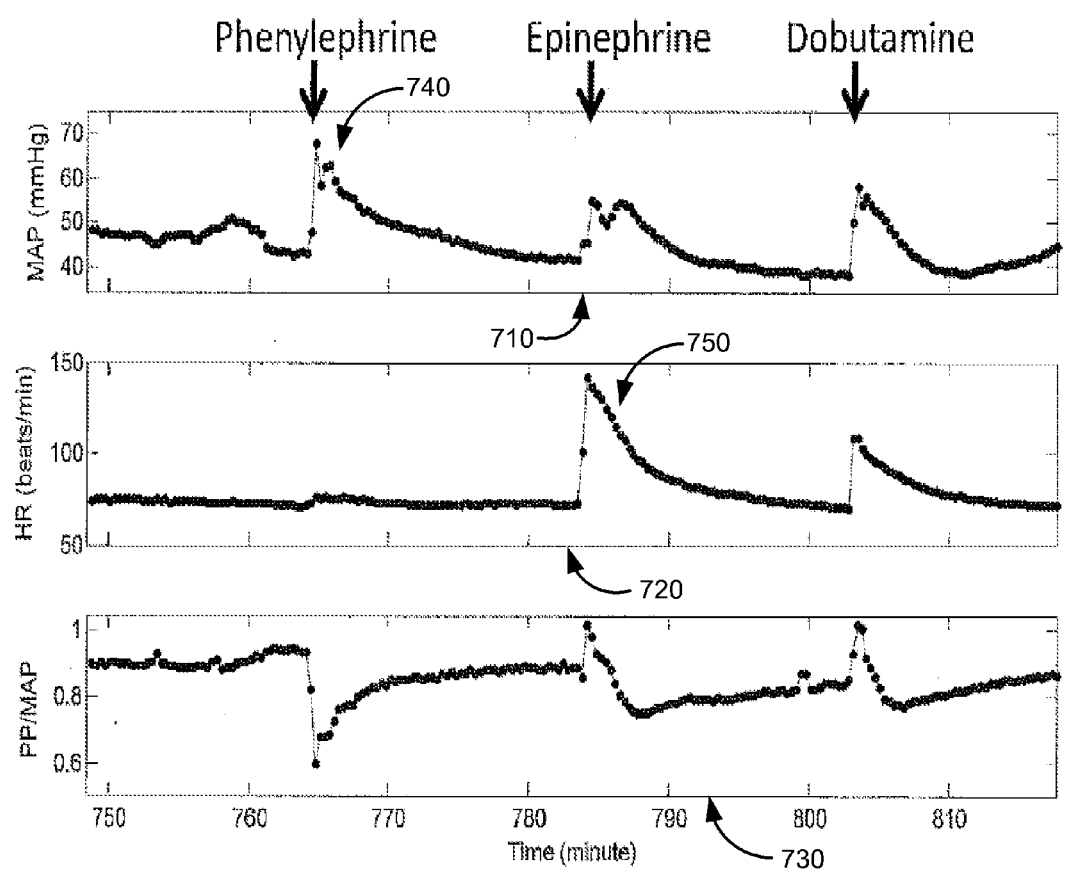
FIGS. 7 and 8 are exemplary patterns that can be used to detect different vasoactive agents.

FIG. 7 shows various input parameters that are graphed with respect to time, and various vasoactive agents that are indicated as being detected at a time t, as soon as threshold values are reached. At 710, a graph is shown with mean arterial pressure (MAP) versus time. At 720, a heart rate (HR) parameter is shown versus time. At 730, a ratio of pulse pressure (PP) to MAP is shown versus time. As can be seen at 740, when phenylephrine is introduced in the blood stream, the heart rate is relatively unchanged, while the PP/MAP ratio decreases and the MAP increases. Thus, using different pulsatility parameters, phenylephrine can be identified. Additionally, analysis of such parameters can be used to distinguish phenylephrine from other vasoactive agents. For example, introduction of epinephrine causes an increase in HR as shown at 750. Additionally, different parameters may have different thresholds. For example, dobutamine can be distinguished from epinephrine by looking at an amount of HR increase, as the HR increase for ephinephrine exceeds that of dobutamine. Thus, using a combination of pulsatility parameters and/or threshold limits, it is possible to distinguish between different vasoactive agents.

Figure 8:
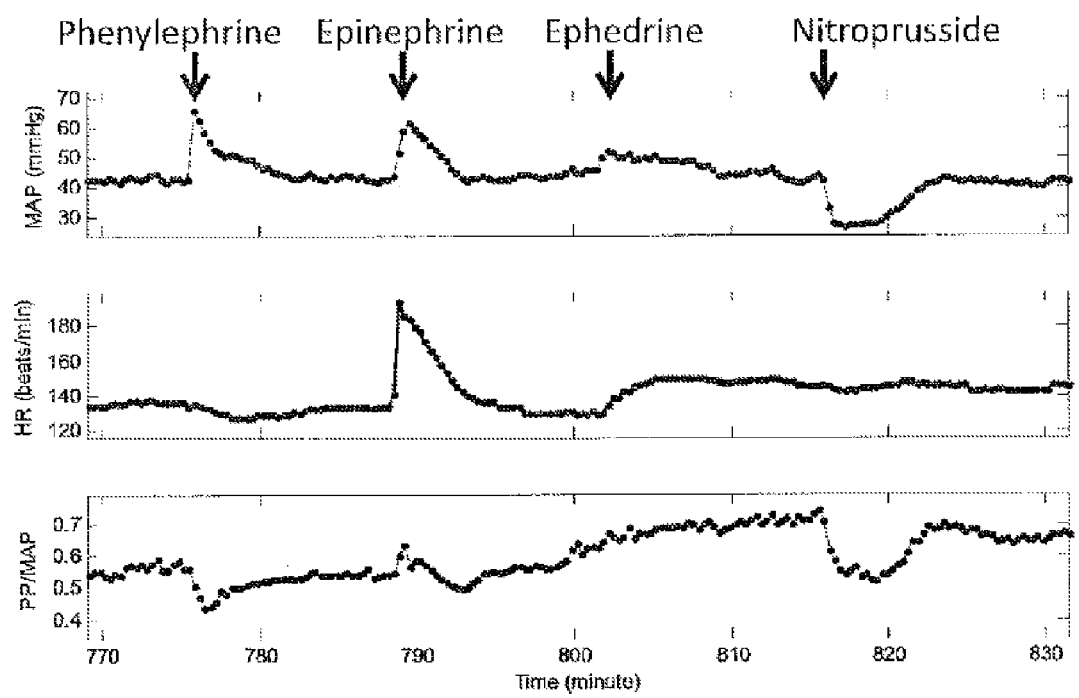

FIG. 8 shows an additional example of vasoactive agents that can be detected using a variety of arterial blood pressure parameters. In this case, phenylephrine, epinephrine, ephedrine, and nitroprusside are detected as being vasoactive agents present in a patient's blood using one or more pulsatility-related parameters. For example, if MAP increases above a predetermined threshold (as an absolute threshold or a differential above a running average), it can be considered that a vasoactive is present, although it can be difficult to know which one. Whereas if a second parameter is used, such as HR, a determination can be made to distinguish phenylephrine from epinephrine. Other vasoactive agents can be distinguished using PP/MAP or other parameters.

Figure 9:
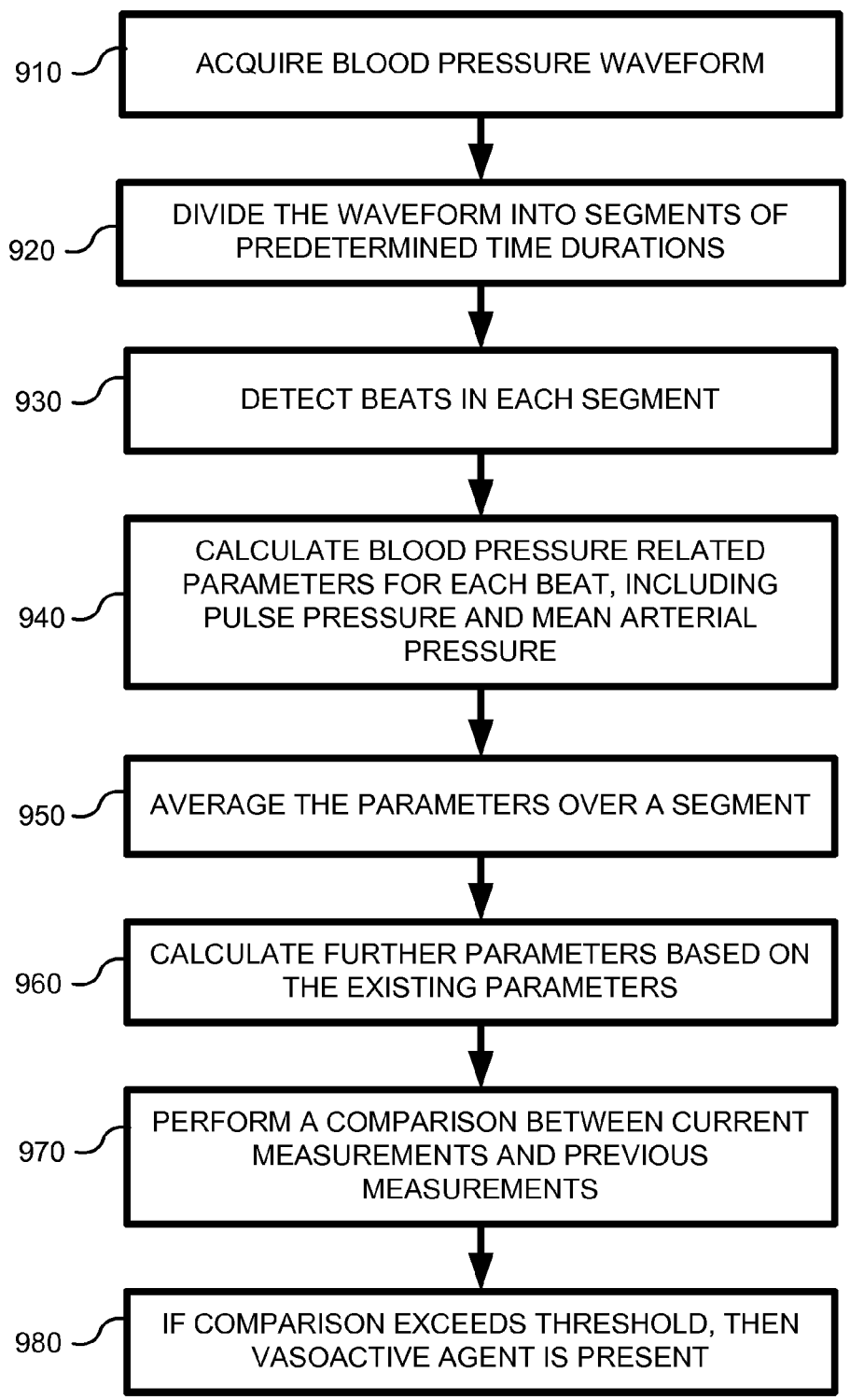
FIG. 9 shows a detailed flowchart of another embodiment for detecting a vasoactive agent.

FIG. 9 shows a flowchart of a method of a detailed embodiment that can be used. In process block 910, a blood pressure waveform is acquired using any of the above-described techniques. In process block 920, the waveform can be divided into segments of predetermined durations (e.g., 20 seconds). In process block 930, each beat in a segment can be detected, such as at the dotted points in FIG. 6. At process block 940, blood pressure related parameters are calculated for each beat. Example parameters are HR, MAP, PP, etc. In process block 950, the parameters are averaged over the segment. In process block 960, further parameters can be calculated based on existing parameters. For example, a ratio of PP to MAP can be calculated. Other ratios can also be calculated and used as parameters. In process block 970, a comparison is performed between current segment measurements and previous segment measurements. In process block 980, if the comparison exceeds a threshold, then a vasoactive agent is present. For example, if $Ratio_{current} < a*Ratio_{prev}$, $HR_{current} = b*HR_{prev}$, $MAP_{current} > c*MAP_{prev}$ then Phenylephrine is present at the current measurement, wherein a, b, and c are predetermined constants. If desired, a hemodynamic parameter can be calculated, wherein the calculation includes using the presence or absence of the vasoactive agent in the determination of the parameter.

Exemplary embodiments of the present invention have been described above with reference to a block diagram of methods, apparatuses, and computer program products. One of skill will understand that each block of the block diagram, and combinations of blocks in the block diagram, respectively, can be implemented by various means including computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the blocks.

The methods described herein further relate to computer program instructions that may be stored in a computer-readable memory that can direct a computer or other programmable data processing apparatus, such as in a processor or processing system, to function in a particular manner, such that the instructions stored in the computer-readable memory produce an article of manufacture including computer-readable instructions for implementing the described methods. Moreover, the various software modules used to perform the various calculations and perform related method steps described herein also can be stored as computer-executable instructions on a computer-readable medium in order to allow the methods to be loaded into and executed by different processing systems.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope of these claims.

We claim:

1. A method of using a patient monitoring system to detect a vasoactive agent in a bloodstream of a patient, the patient monitoring system including a blood pressure sensor, an analog-to-digital converter and a hardware processor configured to execute a software, the method comprising:

sensing, using the blood pressure sensor, a blood pressure of an artery of the patient and generating a blood pressure signal;

receiving, using the analog-to-digital converter, the blood pressure signal and converting the blood pressure signal to blood pressure data in digital form;

receiving, using the hardware processor executing the software, the blood pressure data for each of a plurality of time segments;

calculating, using the hardware processor executing the software, a first pressure parameter (FPP), a heart rate (HR), a second pressure parameter (SPP) and a ratio of the SPP to the FPP (SPP/FPP) for each of the plurality of time segments based on the blood pressure data;

determining, using the hardware processor executing the software, whether or not the bloodstream of the patient includes the vasoactive agent, wherein the bloodstream of the patient includes the vasoactive agent when the FPP increases over the plurality of time segments to exceed a FPP threshold, the HR is considered to remain unchanged over the plurality of time segments, and the SPP/FPP decreases over the plurality of time segments to fall below a SPP/FPP threshold;

obtaining a cardiac output of the patient;

wherein when the determining determines that the bloodstream of the patient includes the vasoactive agent, clinically treating the patient based on a determination that the cardiac output of the patient is inaccurate; and wherein when the determining determines that the bloodstream of the patient does not include the vasoactive agent, clinically treating the patient based on the cardiac output of the patient being accurate.

2. The method of claim 1, wherein the blood pressure signal is a waveform, and wherein the method further comprises dividing the waveform into the plurality of time segments of a predetermined time.

3. The method of claim 1, wherein the sensing by the blood pressure sensor is performed non-invasively.

4. The method of claim 1, wherein the sensing by the blood pressure sensor is performed invasively.

5. The method of claim 1, wherein prior to the calculating, the method further comprises detecting beats in each of the plurality of time segments, and wherein the calculating calculates the FPP, the HR, the SPP and the SPP/FPP for each of the beats in each of the plurality of time segments.

6. The method of claim 1, wherein the FPP includes one or more of a diastolic pressure, a systolic pressure and a mean arterial pressure, and the SPP includes one or more of a standard deviation derived from the blood pressure data and a pulse pressure.

7. A method of using a patient monitoring system to detect a vasoactive agent in a bloodstream of a patient, the patient monitoring system including a presenting device, a blood pressure sensor, an analog-to-digital converter and a hardware processor configured to execute a software, the method comprising:

sensing, using the blood pressure sensor, a blood pressure of an artery of the patient and generate a blood pressure signal;

receiving, using the analog-to-digital converter, the blood pressure signal and converting the blood pressure signal to blood pressure data in digital form;

receiving, using the hardware processor executing the software, the blood pressure data for each of a plurality of time segments;

calculating, using the hardware processor executing the software, a mean arterial pressure (MAP), a heart rate (HR), a pulse pressure (PP) and a ratio of the PP to the MAP (PP/MAP) for each of the plurality of time segments based on the blood pressure data;

determining, using the hardware processor executing the software, whether or not the bloodstream of the patient includes the vasoactive agent, wherein the bloodstream of the patient includes the vasoactive agent when the MAP increases over the plurality of time segments to exceed a MAP threshold, the HR is considered to remain unchanged over the plurality of time segments, and the PP/MAP decreases over the plurality of time segments to fall below a PP/MAP threshold; and obtaining, using the hardware processor executing the software, a hemodynamic parameter, using the blood pressure data, by taking into account whether or not that the bloodstream of the patient includes the vasoactive agent; and clinically treating the patient using the hemodynamic parameter.

8. The method of claim 7, wherein the blood pressure signal is a waveform, and wherein the waveform is divided into the plurality of time segments of a predetermined time.

9. The method of claim 7, wherein the blood pressure sensor senses the blood pressure of the artery of the patient non-invasively.

10. The method of claim 7, wherein the blood pressure sensor senses the blood pressure of the artery of the patient invasively.

11. The method of claim 7, wherein prior to the calculating, the method further comprises detecting beats in each of the plurality of time segments, and wherein the calculating calculates the MAP, the HR, the PP and the PP/MAP for each of the beats in each of the plurality of time segments.

12. The method of claim 7, wherein when the determining determines that the bloodstream of the patient includes the vasoactive agent, clinically treating the patient based on the hemodynamic parameter being inaccurate, and wherein when the determining determines that the bloodstream of the patient does not include the vasoactive agent, clinically treating the patient based on the hemodynamic parameter being accurate.

* * * * *